(12) United States Patent
Furukawa et al.

(10) Patent No.: US 11,490,789 B2
(45) Date of Patent: Nov. 8, 2022

(54) ADHESIVE FOR ENDOSCOPE, CURED PRODUCT, ENDOSCOPE, AND METHOD FOR PRODUCING ENDOSCOPE

(71) Applicant: FUJIFILM Corporation, Tokyo (JP)

(72) Inventors: Kazushi Furukawa, Kanagawa (JP); Toshihide Yoshitani, Kanagawa (JP); Yoshihiro Nakai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 45 days.

(21) Appl. No.: 16/802,103

(22) Filed: Feb. 26, 2020

(65) Prior Publication Data

US 2020/0187754 A1  Jun. 18, 2020

Related U.S. Application Data

(63) Continuation of application No. PCT/JP2018/031542, filed on Aug. 27, 2018.

(30) Foreign Application Priority Data

Aug. 30, 2017 (JP) ............................. JP2017-165917

(51) Int. Cl.
*C09J 163/00* (2006.01)
*A61B 1/00* (2006.01)

(52) U.S. Cl.
CPC ...... *A61B 1/00064* (2013.01); *A61B 1/00128* (2013.01); *C09J 163/00* (2013.01)

(58) Field of Classification Search
CPC ...... C08L 63/00; C09J 63/00; C08G 59/4014; A61B 1/00064
See application file for complete search history.

(56) References Cited

U.S. PATENT DOCUMENTS

| | | | | |
|---|---|---|---|---|
| 3,632,795 A | * | 1/1972 | Thomas et al. | C08L 63/00 528/114 |
| 2007/0129466 A1 | | 6/2007 | Kagawa et al. | |
| 2008/0114205 A1 | | 5/2008 | Kagawa et al. | |
| 2009/0155597 A1 | * | 6/2009 | Kropp | C09J 9/02 428/414 |
| 2011/0245612 A1 | * | 10/2011 | Nakamura | A61B 1/00071 600/139 |
| 2012/0082842 A1 | | 4/2012 | Hirano et al. | |
| 2014/0128669 A1 | | 5/2014 | Kobayashi et al. | |
| 2016/0222261 A1 | * | 8/2016 | Yokoyama | C09J 163/00 |

FOREIGN PATENT DOCUMENTS

| | | |
|---|---|---|
| CN | 101903485 A | 12/2010 |
| CN | 102204806 A | 10/2011 |
| CN | 102471661 A | 5/2012 |
| EP | 1847213 A1 | 10/2007 |
| JP | H11-60694 A | 3/1999 |
| JP | 2002-238834 A | 8/2002 |
| JP | 2002238834 * | 8/2002 |
| JP | 2008-284191 A | 11/2008 |
| JP | 2011-212338 A | 10/2011 |
| JP | 2015-117283 A | 6/2015 |
| WO | 2006/013860 A1 | 2/2006 |

OTHER PUBLICATIONS

JP 2002 238834 machine translation (2002).*
An Office Action; "Decision to Grant a Patent", mailed by the Japan Patent Office dated Sep. 23, 2020, which corresponds to Japanese Patent Application No. 2019-539483 and is related to U.S. Appl. No. 16/802,103; with English language translation.
International Search Report issued in PCT/JP2018/031542; dated Sep. 25, 2018.
International Preliminary Report on Patentability issued in PCT/JP2018/031542 completed Aug. 2, 2019.
The extended European search report issued by the European Patent Office dated Jul. 27, 2020, which corresponds to European Patent Application No. 18851232.1-1107 and is related to U.S. Appl. No. 16/802,103.
An Office Action mailed by China National Intellectual Property Administration dated Oct. 20, 2021 which corresponds to Chinese Patent Application No. 201880051397.3 and is related to U.S. Appl. No. 16/802,103 with English language translation.

* cited by examiner

*Primary Examiner* — Kuo Liang Peng
(74) *Attorney, Agent, or Firm* — Studebaker & Brackett PC

(57) ABSTRACT

Provided are an adhesive for an endoscope, a cured product thereof, an endoscope produced using the adhesive for an endoscope, and a method for producing the endoscope. The adhesive for an endoscope is a two-component adhesive for an endoscope. The two-component adhesive has a base and a curing agent. The base includes at least one epoxy resin (A) selected from the group consisting of bisphenol A epoxy resins, bisphenol F epoxy resins, and phenol novolac epoxy resins. The curing agent includes at least one specific polyamine compound (B). The adhesive for an endoscope is used to fix at least one of a metal member or a glass member constituting the endoscope.

18 Claims, 3 Drawing Sheets

ADHESIVE FOR ENDOSCOPE, CURED PRODUCT, ENDOSCOPE, AND METHOD FOR PRODUCING ENDOSCOPE

CROSS-REFERENCE TO RELATED APPLICATIONS

This application is a Continuation of PCT International Application No. PCT/JP2018/031542 filed on Aug. 27, 2018, which claims priority under 35 U.S.C. § 119 (a) to Japanese Patent Application No. 2017-165917 filed in Japan on Aug. 30, 2017. Each of the above applications is hereby expressly incorporated by reference, in its entirety, into the present application.

BACKGROUND OF THE INVENTION

1. Field of the Invention

The present invention relates to an adhesive for an endoscope, a cured product, an endoscope, and a method for producing an endoscope.

2. Description of the Related Art

Endoscopes for examining human body cavities are repeatedly used. Thus, a flexible tube constituting an insertion section of an endoscope needs to be washed and disinfected with chemicals after each use. To prevent infectious diseases, high cleanliness at the level of sterilization rather than disinfection is required particularly when an endoscope is inserted into a highly susceptible region, such as a bronchus. Accordingly, the use of not only ethylene oxide gas (EOG) sterilization treatment, which is widely practiced, but also treatments having higher sterilization effects has been demanded. For example, JP2011-212338A discloses a flexible tube for an endoscope, the flexible tube including a metal core, an outer cover layer, an adhesion-improving layer formed around the outer circumference of the outer cover layer and containing a soft epoxy resin, and an overcoat layer formed around the outer circumference of the adhesion-improving layer. This flexible tube for an endoscope is highly durable such that if it is subjected to an autoclave sterilization treatment and a hydrogen peroxide plasma sterilization treatment, the outer cover is less likely to break or deteriorate, and required flexibility and protection are maintained.

The insertion section of an endoscope is inserted into a body cavity through the oral cavity or nasal cavity. To alleviate foreign body sensation and pain in patients during the insertion, the insertion section of an endoscope desirably has a smaller diameter. Thus, instead of bulky members such as screws, adhesives are mainly used to stack and bond together members constituting the insertion section including a metal core, an outer cover layer, and others as described above. JP2015-117283A discloses an adhesive composition for a medical device, the adhesive composition containing an epoxy resin and a modified silicone. This adhesive composition for a medical device can provide a medical device that has high sterilization resistance even after repeated sterilization treatments and can satisfactorily maintain the adhesive strength and appearance of an adhesive layer of the medical device.

SUMMARY OF THE INVENTION

Of the sterilization treatments, the hydrogen peroxide plasma sterilization treatment is a method involving decomposing hydrogen peroxide with plasma to generate hydroxyl radicals and achieving sterilization through the action of the hydroxyl radicals. The hydrogen peroxide plasma sterilization treatment is powerful sterilization means. This treatment, however, induces a decrease in performance of an endoscope as described below when a metal member, an optical member, or the like constituting the endoscope is, for example, fixed (bonded) using an adhesive (epoxy adhesive) containing an epoxy resin as a base.

That is, a cured product of a commonly used epoxy adhesive is generally prone to oxidation degradation due to hydrogen peroxide. Thus, when an epoxy adhesive is used for fixation of a glass member constituting an optical system composed of objective lenses and the like in a tip portion of an endoscope, a cured product of the epoxy adhesive is likely to undergo discoloration, clouding, and the like as a result of oxidation degradation due to a hydrogen peroxide plasma sterilization treatment. This discoloration or clouding may cause a decrease in optical performance of the endoscope (performance of the objective lenses and the like). Furthermore, while the epoxy adhesive is typically used, in the tip portion of the endoscope, for fixation of a metal member such as stainless steel in many cases, the hydrogen peroxide plasma sterilization treatment causes dissociation of metal ions, and the dissociated metal ions further promote the oxidation degradation of the cured product of the epoxy adhesive. As a result, the state of the metal member fixed with the epoxy adhesive is easily destabilized by the hydrogen peroxide plasma sterilization treatment.

Accordingly, an adhesive used, for example, for fixation of a metal member or a glass member of an endoscope is required to have higher oxidation resistance and higher degradation resistance (durability) against hydrogen peroxide plasma sterilization treatment.

To reduce the burden on subjects, the diameter of the insertion section to be inserted into a body cavity has been increasingly reduced as described above. As the diameter of the insertion section decreases, portions to be bonded together become minuter (thinner or smaller), and thus adhesives used for fixation are required to have physical properties that facilitate injection or application, for example, into an interstitial minute portion.

An object of the present invention is to provide an adhesive for an endoscope and a cured product thereof, the adhesive being highly suitable for injection or application into a minute portion such that the above various and high-level requirements for the use for an endoscope are satisfied and being less likely to undergo oxidization degradation when subjected to a hydrogen peroxide plasma sterilization treatment in the state of being used for fixation of a member (the state of being bonded to the member and cured). Another object of the present invention is to provide an adhesive for an endoscope and a cured product thereof, the adhesive being able to maintain high adhesiveness when subjected to a hydrogen peroxide plasma sterilization treatment in the state of being used for fixation of a metal member to a resin member (the state of being bonded to the metal member and cured), the adhesive being suitable for fixation of a metal member or a glass member constituting the endoscope. Still another object of the present invention is to provide an endoscope that has the cured product as a member for fixing a member constituting the endoscope and that is less likely to undergo degradation in performance when subjected to a hydrogen peroxide plasma sterilization treatment. Still another object of the present invention is to provide an endoscope produced using the adhesive for an endoscope. Still another object of the present invention is to provide a method for producing an endoscope by using the adhesive for an endoscope.

The above objects have been achieved by the following means.

<1> A two-component adhesive for an endoscope has a base and a curing agent.

The base includes at least one epoxy resin (A) selected from the group consisting of bisphenol A epoxy resins, bisphenol F epoxy resins, and phenol novolac epoxy resins.

The curing agent includes at least one polyamine compound (B) represented by general formula (I) or (II) below.

The adhesive for an endoscope is used to fix at least one of a metal member or a glass member (a metal member and/or a glass member) constituting the endoscope.

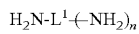  general formula (I)

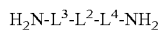  general formula (II)

In general formula (I), n represents an integer of 1 to 3. $L^1$ represents an aliphatic or alicyclic hydrocarbon group with a valence of (n+1), an aromatic hydrocarbon group with a valence of (n+1), or a group with a valence of (n+1) having an aliphatic hydrocarbon chain into which at least one oxygen atom is incorporated. When n is 1 and the hydrocarbon group is an alicyclic saturated hydrocarbon group, the alicyclic saturated hydrocarbon group does not include a quaternary carbon atom as an annular atom.

In general formula (II), $L^2$ represents an alkylene group having 2 or more carbon atoms, —O—, or a divalent group having a combination thereof, and $L^3$ and $L^4$ each independently represent an arylene group.

<2> The adhesive for an endoscope according to <1> is used to fix a member in a tip portion of an insertion section of the endoscope.

<3> The adhesive for an endoscope according to <2> is used to seal peripheries of an observation window and an illumination window in the tip portion of the insertion section of the endoscope.

<4> The adhesive for an endoscope according to <2> is used to fix a prism in an optical device constituting the endoscope.

<5> The adhesive for an endoscope according to any one of <1> to <4> is used in the form of a mixture of the base and the curing agent with the polyamine compound (B) being present in an amount of 10 to 75 parts by mass based on 100 parts by mass of the epoxy resin (A).

<6> A cured product is formed by curing the adhesive for an endoscope according to any one of <1> to <5>.

<7> An endoscope includes the cured product according to <6>. The cured product fixes at least one of a metal member or a glass member.

<8> A method for producing an endoscope includes fixing at least one of a metal member or a glass member by using the adhesive for an endoscope according to any one of <1> to <5>.

In the description of the present invention, the expression "to" is meant to include the numerical values before and after "to" as the lower and upper limits.

In the description of the present invention, when the number of carbon atoms of a group is specified, the number of carbon atoms means the number of carbon atoms of the whole group. That is, when the group further has a substituent, the number of carbon atoms means the number of carbon atoms of the whole including the substituent.

The adhesive for an endoscope according to the present invention is highly suitable for injection or application into a minute portion used in a configuration of a flexible tube for an endoscope, is less likely to undergo oxidation degradation when subjected to a hydrogen peroxide plasma sterilization treatment in the state of being used for fixation of a member, and is able to maintain high adhesiveness when subjected to a hydrogen peroxide plasma sterilization treatment in the state of being used for fixation of a metal member. Thus, the adhesive for an endoscope according to the present invention is suitable for fixing a metal member or a glass member constituting the endoscope. The cured product according to the present invention is less likely to undergo oxidization degradation when subjected to a hydrogen peroxide plasma sterilization treatment. Therefore, the endoscope according to the present invention, which has the cured product as a member for fixing a metal member or a glass member, is also less likely to undergo degradation in performance when subjected to a hydrogen peroxide plasma sterilization treatment. According to the method for producing an endoscope according to the present invention, the above-described endoscope can be provided.

DESCRIPTION OF THE PREFERRED EMBODIMENTS

Adhesive for Endoscope

Figure 1:
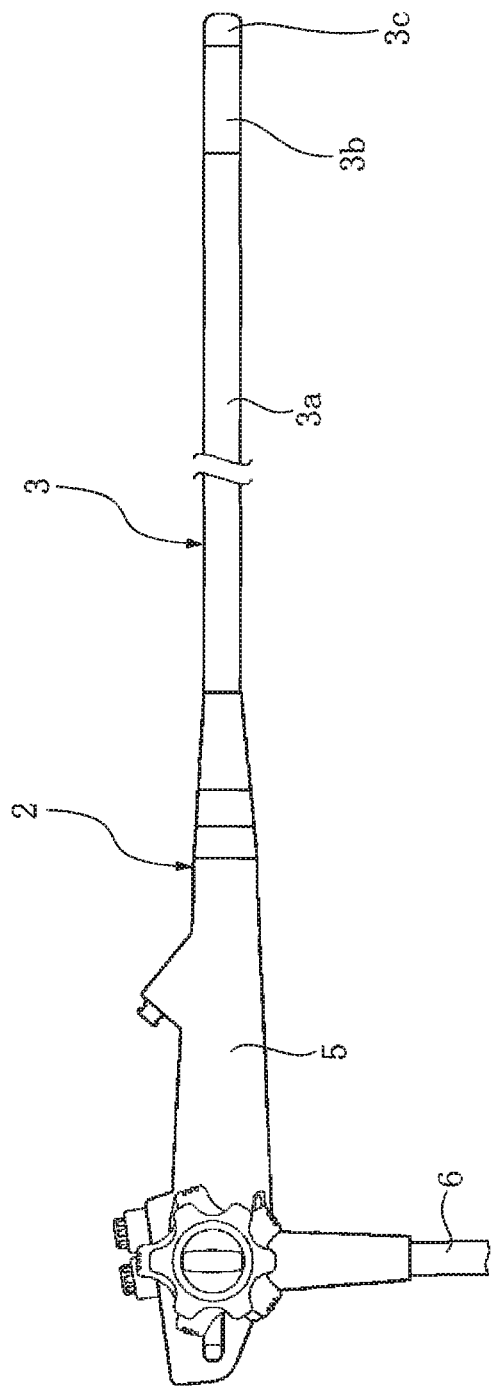
FIG. 1 is an external view illustrating a configuration of an endoscope according to an embodiment of the present invention.

An adhesive for an endoscope according to the present invention is a two-component adhesive that includes a base and a curing agent separate from each other (that is composed of a formulation including the base and a formulation including the curing agent).

The base includes at least one epoxy resin (A) selected from the group consisting of bisphenol A epoxy resins, bisphenol F epoxy resins, and phenol novolac epoxy resins, and the curing agent includes at least one polyamine compound (B) represented by general formula (I) or (II) given later.

The adhesive for an endoscope according to the present invention is used to fix at least one of a metal member or a glass member constituting the endoscope. The "fixing" is performed by bonding at least one of the metal member or the glass member to, for example, a supporting member constituting the endoscope. The supporting member may be a tube wall or the like of the endoscope or an immovable member fixed to the tube wall or the like, or may be a member whose relative position in the endoscope can be moved like a tube. In the present invention, the term "fixing" is meant to include filling, that is, sealing, with a cured adhesive, a space between at least one of the metal member or the glass member constituting the endoscope, and the supporting member incorporated with the metal member or the glass member.

Hereinafter, the "adhesive for an endoscope" may be referred to simply as the "adhesive". A fixing portion or a sealing portion formed of the above cured adhesive between a member and a member may be referred to as an adhesive joint.

The adhesive according to the present invention is highly suitable for injection or application into a minute portion. That is, the adhesive according to the present invention can be smoothly injected into a minute portion of a constituent member of an endoscope. A cured product formed by curing the adhesive is less likely to undergo oxidization degradation when subjected to a hydrogen peroxide plasma sterilization treatment. Therefore, an endoscope produced using the adhesive according to the present invention is less likely to undergo performance degradation when repeatedly subjected to a hydrogen peroxide plasma sterilization treatment. Although not clear, the reasons for this are probably as follows.

The polyamine compound (B) constituting the curing agent is unlikely to interact with the epoxy resin (A) constituting the base, and when the base and the curing agent are mixed together, the mixture can stay in a low-viscosity state for a while. This is probably one of the reasons that the suitability for injection or application into a minute portion is high. Meanwhile, a crosslinked structure formed by the epoxy resin (A) and the polyamine compound (B) is composed of an amine structure, a hydrocarbon structure, and a hydroxy group and, unlike polyamidoamines, does not have an amide bond, which is considered to react and decompose upon hydrogen peroxide plasma sterilization treatment. This is probably because the adhesive joint having high sterilization resistance can be formed.

The adhesive according to the present invention has high suitability for thick coating probably because the adhesive, when used, gradually hardens and becomes more viscous.

Epoxy Resin (A)

The epoxy resin (A) used in the present invention includes at least one of a bisphenol A epoxy resin, a bisphenol F epoxy resin, or a phenol novolac epoxy resin (a bisphenol A epoxy resin, a bisphenol F epoxy resin, and/or a phenol novolac epoxy resin). These epoxy resins may be used alone or may be used in combination.

The bisphenol A epoxy resin used in the present invention is not particularly limited and may be any bisphenol A epoxy resin commonly used as a base of an epoxy adhesive. Specific examples include bisphenol A diglycidyl ethers (e.g., "jER825", "jER828", and "jER834" (trade names) manufactured by Mitsubishi Chemical Corporation) and bisphenol A propoxylate diglycidyl ethers.

The bisphenol F epoxy resin used in the present invention is not particularly limited and may be any bisphenol F epoxy resin commonly used as a base of an epoxy adhesive. Specific examples include bisphenol F diglycidyl ethers (e.g., "EPICLON 830" (trade name) manufactured by DIC Corporation) and 4,4'-methylenebis(N,N-diglycidylaniline).

The phenol novolac epoxy resin used in the adhesive according to the present invention is not particularly limited and may be any phenol novolac epoxy resin commonly used as a base of an epoxy adhesive. Specific examples include product number 406775 manufactured by Sigma-Aldrich.

Polyamine Compound (B)

The adhesive according to the present invention contains at least one polyamine compound (B) represented by general formula (I) or (II) below.

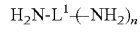 general formula (I)

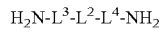 general formula (II)

In general formula (I), n represents an integer of 1 to 3. $L^1$ represents an aliphatic or alicyclic hydrocarbon group with a valence of (n+1), an aromatic hydrocarbon group with a valence of (n+1), or a group with a valence of (n+1) having an aliphatic hydrocarbon chain into which at least one oxygen atom is incorporated (i.e., an aliphatic hydrocarbon group with a valence of (n+1) whose aliphatic hydrocarbon chain has at least one oxygen atom incorporated thereinto). When n is 1 and the hydrocarbon group is an alicyclic saturated hydrocarbon group, the alicyclic saturated hydrocarbon group does not include a quaternary carbon atom as an annular atom. "Quaternary carbon atom" means a carbon atom to which no hydrogen atoms are bonded.

In general formula (II), $L^2$ represents an alkylene group having 2 or more carbon atoms, —O—, or a divalent group having a combination thereof, and $L^3$ and $L^4$ each independently represent an arylene group.

The polyamine compounds do not include "—O—O—".

When n is 1, the divalent aliphatic or alicyclic hydrocarbon group represented by $L^1$ is preferably an alkylene group, and the divalent group represented by $L^1$ and having an aliphatic hydrocarbon chain into which at least one oxygen atom is incorporated is preferably a group formed by combining a poly(oxyalkylene) group and an alkylene group.

When n is 2, the trivalent aliphatic or alicyclic hydrocarbon group represented by $L^1$ is preferably an alkanetriyl group, and the trivalent group represented by $L^1$ and having an aliphatic hydrocarbon chain into which at least one oxygen atom is incorporated is preferably a trivalent group formed by combining an alkanetriyl group and three poly(oxyalkylene) groups.

When n is 3, the tetravalent aliphatic or alicyclic hydrocarbon group represented by $L^1$ is preferably an alkanetetrayl group, and the tetravalent group represented by $L^1$ and having an aliphatic hydrocarbon chain into which at least one oxygen atom is incorporated is preferably a tetravalent group formed by combining an alkanetetrayl group and four poly(oxyalkylene) groups.

n is preferably 1 or 2, more preferably 1.

The alkylene group may be linear or cyclic. Cyclic alkylene groups include alkylene groups including a saturated alicycle. The number of carbon atoms of the alkylene group is preferably 1 to 20, more preferably 5 to 12. Specific examples of the alkylene group include methylene, ethylene, hexamethylene, 2,2,4-trimethylhexamethylene, 2-methylpentamethylene, cyclohexylene, dodecamethylene, and methylene-cyclohexylene-methylene. Specific examples of "alkylene groups including a saturated alicycle" include methylene-cyclohexylene-methylene.

The alkylene group of an oxyalkylene group of a poly(oxyalkylene) group is as defined for the above alkylene group. The number of carbon atoms of the alkylene group of an oxyalkylene group is preferably 1 to 20, more preferably 1 to 5, still more preferably 1 to 3. The number of repetitions of the oxyalkylene group is preferably an integer of 1 to 20. The polyamine compound represented by general formula (I) above may include a plurality of compounds different in the number of repetitions of the oxyalkylene group. When the compound has a plurality of poly(oxyalkylene) groups, the plurality of poly(oxyalkylene) groups may be the same or different in structural unit and the number of repetitions.

The number of carbon atoms of the aromatic hydrocarbon group is preferably 6 to 14, more preferably 6 to 10. Specific examples of divalent aromatic hydrocarbon groups (arylene groups) include phenylene and naphthylene. Specific examples of trivalent aromatic hydrocarbon groups (arenetriyl groups) include benzenetriyl and naphthalenetriyl.

Specific examples of tetravalent aromatic hydrocarbon groups (arenetetrayl groups) include benzenetetrayl and naphthalenetetrayl.

The alkanetriyl group may be linear or cyclic. Cyclic alkanetriyl groups include alkanetriyl groups including a saturated alicycle. The number of carbon atoms of the alkanetriyl group is preferably 1 to 20, more preferably 1 to 15, particularly preferably 1 to 10. Examples include methanetriyl, ethanetriyl, propanetriyl, butanetriyl, t-butanetriyl, and cyclohexanetriyl. Specific examples of "alkanetriyl groups including a saturated alicycle" include alkanetriyl groups formed by combining a cyclohexanetriyl group and three methylene groups.

The alkanetetrayl group may be linear or cyclic. Cyclic alkanetetrayl groups include alkanetetrayl groups including a saturated alicycle. The number of carbon atoms of the alkanetetrayl group is preferably 1 to 20, more preferably 1 to 15, particularly preferably 1 to 10. Examples include methanetetrayl, ethanetetrayl, propanetetrayl, t-butanetetrayl, and cyclohexanetetrayl. Specific examples of "alkanetetrayl groups including a saturated alicycle" include alkanetetrayl groups formed by combining a cyclohexanetetrayl group and four methylene groups.

The alkylene group having 2 or more carbon atoms represented by $L^2$ may be linear or cyclic. Cyclic alkylene groups include alkylene groups including a saturated alicycle. The number of carbon atoms of the alkylene group is preferably 2 to 20, more preferably 2 to 12. Specific examples of the alkylene group having 2 or more carbon atoms include ethylene, hexamethylene, 2,2,4-trimethylhexamethylene, 2-methylpentamethylene, cyclohexylene, dodecamethylene, and methylene-cyclohexylene-methylene.

The arylene groups represented by $L^3$ and $L^4$ are as defined for the above divalent aromatic hydrocarbon groups (arylene groups), and preferred ranges thereof are also the same as those of the above divalent aromatic hydrocarbon groups.

$L^1$ to $L^4$ may each have a substituent, and specific examples of the substituent include alkyl groups. The number of carbon atoms of the alkyl groups is preferably 1 to 12, more preferably 1 to 8, particularly preferably 1 to 5. Specific examples of the alkyl groups include methyl, ethyl, n-butyl, isopropyl, s-butyl, t-butyl, t-pentyl, t-hexyl, and t-octyl. Of these, methyl is preferred. The number of carbon atoms of the groups defined by $L^1$ to $L^4$ above includes the number of carbon atoms of the substituents that $L^1$ to $L^4$ may have.

The molecular weight of $L^1$ is preferably 60 to 1000, more preferably 80 to 500.

The molecular weight of $L^3$-$L^2$-$L^4$ is preferably 180 to 1000, more preferably 180 to 500.

When $L^1$ to $L^4$ have a substituent, the molecular weight of the substituent is also included in the above molecular weight.

The polyamine compound (B) in the present invention preferably contains at least the polyamine compound (B) represented by general formula (I). The polyamine compound (B) represented by general formula (I) is unlikely to react with hydroxyl radicals generated upon ethylene oxide gas sterilization treatment or hydrogen peroxide plasma sterilization treatment and has higher sterilization resistance, and thus the following embodiments are more preferred.

When n=1, $L^1$ preferably represents an alkylene group.
When n=2, $L^1$ preferably represents an alkanetriyl group.
When n=3, $L^1$ preferably represents an alkanetetrayl group.

In the above preferred embodiments, when the alkylene group, the alkanetriyl group, and the alkanetetrayl group represented by $L^1$ are linear, the polyamine compound (B) has high solubility in the base, and the suitability of the adhesive for injection or application into a minute portion can be further improved.

In the above preferred embodiments, when the alkylene group, the alkanetriyl group, and the alkanetetrayl group represented by $L^1$ are cyclic, the crosslink density of the polyamine compound (B) is improved, and the resistance of the cured adhesive to hydrogen peroxide plasma sterilization treatment can be further improved.

Specific examples of polyamine compounds (B) used in the present invention will be described below, but the present invention is not limited thereto. In the following chemical structures, n, x, y, and z each represent the average number of repetitions.

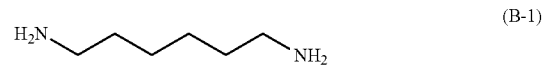

(B-1)

(B-2)

(B-3)

(B-4)

(B-5)

(B-6)

n=6.1

(B-7)

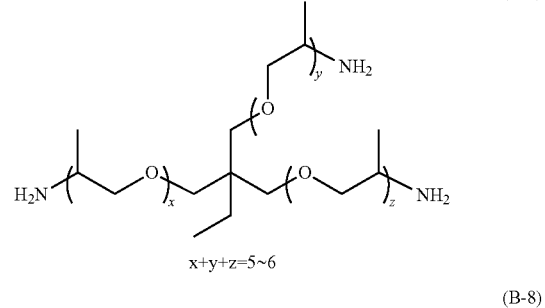

x+y+z=5~6

(B-8)

(B-9)

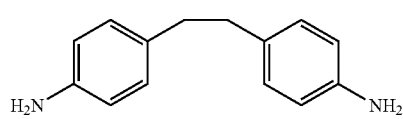
(B-10)

The adhesive according to the present invention is preferably used in the form of a mixture of the epoxy resin (A) constituting the base and the polyamine compound (B) constituting the curing agent such that the mass of active hydrogen is 0.1 to 1.5 equivalents, more preferably 0.3 to 1.0 equivalent, particularly preferably 0.5 to 1.0 equivalent, relative to the epoxy equivalent.

The adhesive according to the present invention is preferably used in the form of a mixture of 100 parts by mass of the epoxy resin (A) constituting the base and 10 to 75 parts by mass, more preferably 10 to 50 parts by mass, of the polyamine compound (B) constituting the curing agent.

When the amount of curing agent used is in the above range, the suitability of the adhesive for injection or application into a minute portion can be further improved. Furthermore, the cured product obtained by curing the adhesive can be provided with high sterilization resistance.

The content of the epoxy resin (A) in the base is preferably 80 mass % or more, more preferably 90 mass % or more, and may be 100 mass %. The base may include at least one of an epoxy resin other than the epoxy resin (A), a solvent, a plasticizer, an adhesion improver (e.g., a silane coupling agent), a surfactant, a colorant (e.g., a pigment, a dye), a weathering agent, an antioxidant, a heat stabilizer, a lubricant, an antistatic agent, a whitener, a release agent, a conductive agent, a viscosity regulator, a filler (e.g., silica, calcium carbonate), a thixotropy-imparting agent, a diluent, or a flame retardant as long as the effects of the present invention are not impaired.

In the present invention, the polyamine compound (B) functions as a curing agent of an epoxy adhesive. Thus, the polyamine compound (B) accounts for preferably 80 mass % or more, more preferably 90 mass % or more, of a curing component (a component that acts on the epoxy resin to cure it) in the curing agent. The polyamine compound (B) may account for all of the curing component in the curing agent. When the curing agent includes a curing component other than the polyamine compound (B), the curing component may be any curing agent or curing aid known as a curing component of an epoxy adhesive. For example, at least one of an acid anhydride compound, an imidazole compound, a phosphorus compound, a thiol compound, a dicyandiamide compound, or a phenolic compound may be used in combination with the polyamine compound (B).

The curing agent may be composed of the above-described curing component or may include, in addition to the above-described curing component, a solvent, a filler, a plasticizer, a viscosity modifier, and the like as long as the effects of the present invention are not impaired. The content of the curing component in the curing agent is preferably 80 mass % or more, more preferably 90 mass % or more.

Cured Product

A cured product according to the present invention is formed by curing the adhesive according to the present invention. That is, the cured product according to the present invention is used as a member constituting an adhesive joint of an endoscope. The cured product according to the present invention can be obtained by mixing the base and the curing agent of the adhesive according to the present invention and then curing the mixture, for example, by heating at 25° C. to 120° C. for 0.5 to 48 hours. The mixing of the base and the curing agent may be performed in the usual manner. The mixing is preferably performed while removing bubbles, and thus is usually performed under reduced pressure.

Endoscope

An endoscope according to the present invention has an adhesive joint between a fixed member and a metal member or a glass member, the adhesive joint being formed of the cured product according to the present invention.

An example of the endoscope (electronic endoscope) according to the present invention will be described. Electronic endoscopes are incorporated with a flexible tube for an endoscope (hereinafter a flexible tube for an endoscope may be referred to simply as a "flexible tube") and are widely used as medical instruments. In the example illustrated in FIG. 1, an electronic endoscope 2 includes an insertion section 3 to be inserted into a body cavity, a main-body operation section 5 connected to the proximal end portion of the insertion section 3, and a universal cord 6 to be connected to a processor device or a light source device. The insertion section 3 is composed of a flexible tube 3a connected to the main-body operation section 5, an angle portion 3b connected to the flexible tube 3a, and a tip portion 3c connected to the distal end of the angle portion 3b and mainly formed of a metal (e.g., stainless steel) member. An imaging device (not illustrated) for imaging a body cavity is built in the tip portion 3c. The flexible tube 3a, which occupies most of the length of the insertion section 3, is flexible over substantially the entire length thereof. In particular, a portion to be inserted into a body cavity or the like has a more flexible structure.

In FIG. 1, a plurality of channels (not illustrated) are formed that extend from the main-body operation section 5 to the distal end surface of the tip portion 3c through the insertion section 3 along the axis direction of the insertion section 3.

Figure 2:
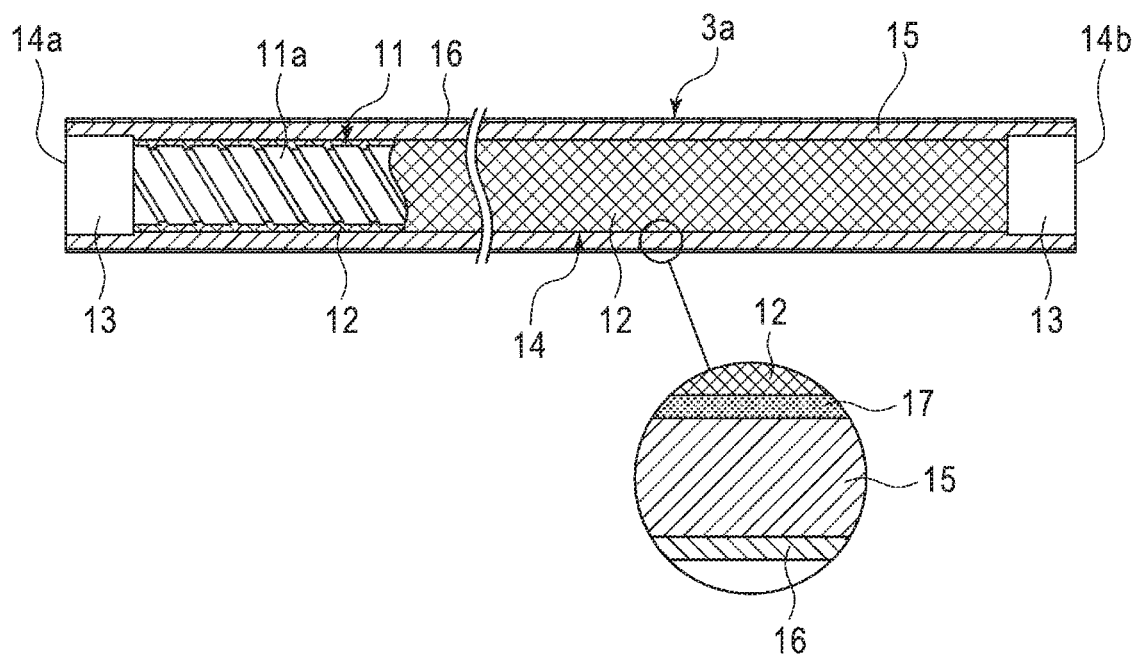
FIG. 2 is a partial sectional view illustrating a configuration of an insertion section of the endoscope illustrated in FIG. 1.

The flexible tube 3a in FIG. 1 is configured such that a resin layer 15 covers the outer peripheral surface of a flexible tube substrate 14, as illustrated in FIG. 2.

14a is the distal side (the tip portion 3c side), and 14b is the proximal side (the main-body operation section 5 side).

The flexible tube substrate 14 includes a spiral tube 11, which is disposed on the innermost side and formed by spirally winding a metal strip 11a, and a tubular net 12, which covers the spiral tube 11 and is formed by braiding metal wires. Caps 13 are fitted to opposite ends of the flexible tube substrate 14. The resin layer 15 is bonded to the flexible tube substrate 14 with a cured adhesive layer 17 interposed therebetween. While the cured adhesive layer (adhesive joint) 17 is illustrated as a layer having a uniform thickness for convenience of illustration, the cured adhesive layer 17 need not necessarily be in such a form and may be indeterminately interposed between the resin layer 15 and the flexible tube substrate 14. The cured adhesive layer 17 may rather have substantially no thickness such that the resin layer 15 and the flexible tube substrate 14 are substantially directly bonded together.

The outer surface of the resin layer 15 is coated with a coat layer 16 having chemical resistance and containing, for example, fluorine. To clearly illustrate the layer structure, the cured adhesive layer 17, the resin layer 15, and the coat layer 16 are illustrated as being thick relative to the diameter of the flexible tube substrate 14.

Figure 3:
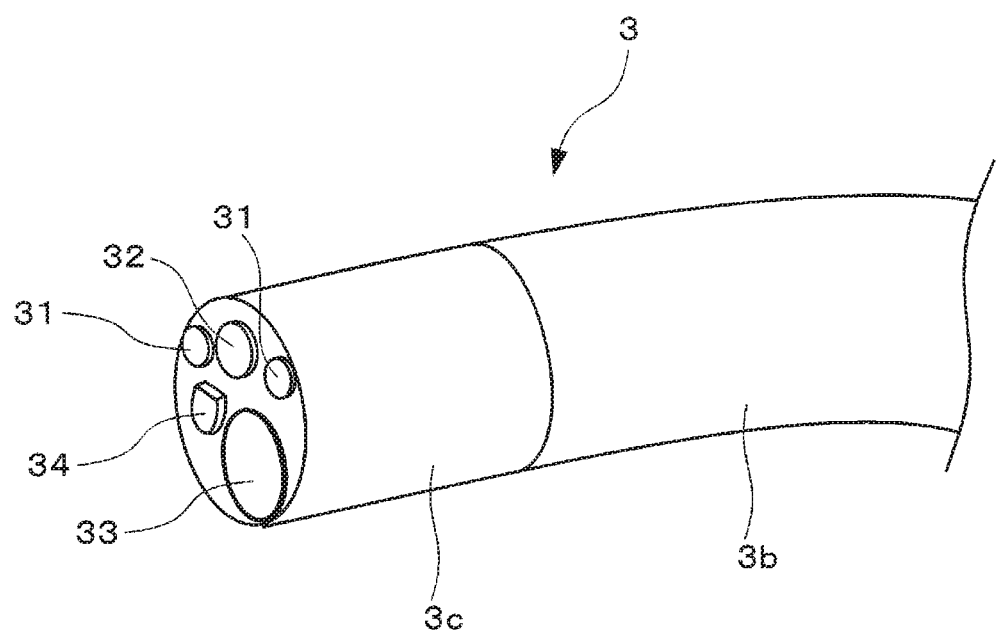
FIG. 3 is an external perspective view of a tip portion of the insertion section.

As illustrated in FIG. 3, an illumination window 31, an observation window 32, and a forceps port 33 are formed in the distal end surface of the tip portion 3c. To wash the distal end surface as required, a nozzle 34 for sending water and air is formed. The illumination window 31, the observation window 32, the forceps port 33, and the nozzle 34 communicate with the main-body operation section 5 through the channels.

Figure 4:
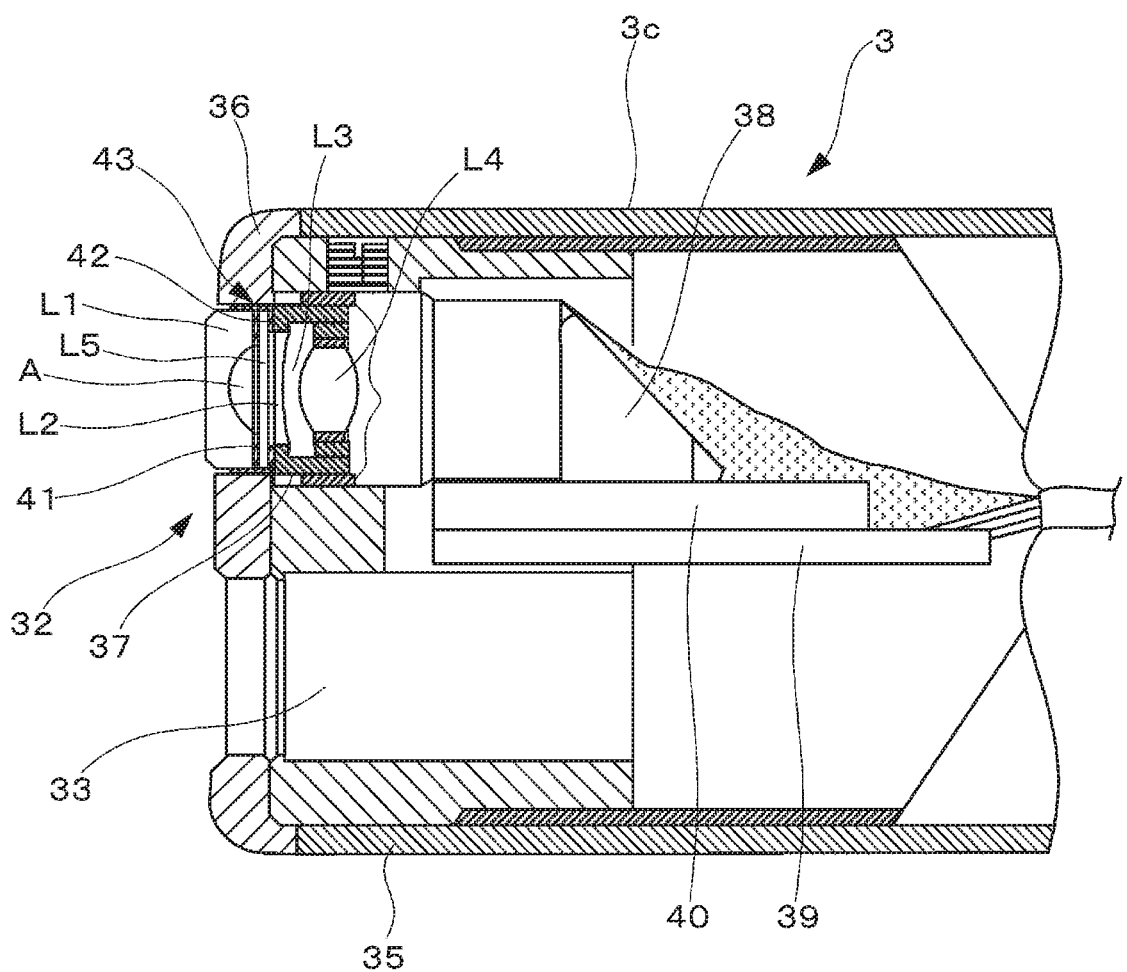
FIG. 4 is a partially cut-away partial sectional view of the tip portion, without hatching that shows sections of lenses and a prism.

As illustrated in FIG. 4, the tip portion 3c is composed of a tip-portion main body 35 made of metal and an end cap 36 made of an electrically insulating material.

An observation unit 43, which is an optical device, is disposed in the observation window 32. The observation unit 43 includes a lens holder 37, and in the lens holder 37, an objective optical system composed of lenses L1 to L5 is fixed with cured adhesives 41 and 42. In the objective optical system. A is an air layer. A prism 38 is bonded and fixed to an end face of the lens holder 37. The optical axis of the objective optical system can be bent at a right angle by the prism 38. The prism 38 is bonded to a solid-state imaging element 40. The solid-state imaging element 40 is fixed to a substrate 39.

Method for Producing Endoscope

A method for producing an endoscope according to the present invention is not particularly limited as long as fixing at least one of a metal member or a glass member by using the adhesive according to the present invention is included. For steps other than fixing of at least one of a metal member or a glass member, usual production steps may be employed to produce the endoscope according to the present invention. For example, the method for producing an endoscope according to the present invention preferably includes a step of mixing the base and the curing agent of the adhesive according to the present invention under reduced pressure, then injecting or applying the adhesive according to the present invention into a target portion, and heating the adhesive at 25° C. to 80° C. for 0.5 to 24 hours.

Use of Adhesive

The adhesive according to the present invention is used to fix at least one of a metal member or a glass member constituting an insertion section of an endoscope to another member constituting the endoscope. That is, the fixing is performed by bonding at least one of the metal member or the glass member to a supporting member (e.g., a member made of resin or rubber, a glass member, or a metal member). Specific examples of how the adhesive according to the present invention is used will be described below, but the present invention is not limited to these examples.

The metal member is not particularly limited. For example, iron-containing metal members such as stainless steel are often used for endoscopes, and the adhesive according to the present invention adheres very well to such metal members.

Examples of members made of resin or rubber include tubes inserted into an insertion section of an endoscope. The tubes include various tubes produced using various materials such as fluorocarbon resins such as Teflon (registered trademark), resins such as polysulfone resins, polyester resins, polyolefin resins, and silicone resins, and rubber. The adhesive according to the present invention can be used, for example, to bond a metal member or a glass member constituting an insertion section of an endoscope to any of the above tubes (to fix the metal member or the glass member to any of the above tubes).

The adhesive according to the present invention can also be used to form the cured adhesive layer 17 in FIG. 2.

The adhesive according to the present invention is preferably used for the tip portion 3c. Among the uses for the tip portion 3c, the adhesive according to the present invention is preferably used to seal the illumination window 31 and the observation window 32 (to fix the glass members). In the sealing, thickly forming adhesive layers around the peripheries of the illumination window 31 and the observation window 32 can smoothen the outer corners of the lenses.

The adhesive according to the present invention can be used to fix at least one of a metal member or a glass member, for example, to assemble the imaging device built in the tip portion 3c, to bond parts together, or to seal the solid-state imaging element 40. The imaging device has an optical system composed of a plurality of optical parts, such as the lenses L1 to L5 and the prism 38, and has the solid-state imaging element 40, such as a charge coupled device (CCD), that photoelectrically converts an optical image formed by the optical system into an imaging signal. The adhesive according to the present invention can be used, for example, to bond together optical parts, such as the lenses L1 to L5 and the prism 38 made of materials such as glass, to bond the prism to a cover glass that protects the CCD, and to bond the prism 38 to the substrate made of resin or metal. This bonding can fix the glass members and can fix the metal member.

The adhesive according to the present invention can be used to bond a stainless-steel tube inside the forceps port. This bonding can fix the metal to the member made of metal.

The adhesive according to the present invention can be used for bond-fixing and sealing of the solid-state imaging element 40 and the substrate 39. This bonding can fix the metal members constituting the solid-state imaging element, the substrate, and the like.

The adhesive according to the present invention can be used, for example, to bond the tip portion 3c to the angle portion 3b.

EXAMPLES

The present invention will now be described in more detail with reference to examples. These examples should not be construed as limiting the present invention. "Room temperature" means 25° C.

Preparation of Base/Curing Agent Mixture of Adhesive for Endoscope (Example 1)

Using a "THINKY MIXER ARV-310 (trade name, manufactured by THINKY CORPORATION)", 100 parts by mass of an epoxy resin (A-1) (bisphenol A diglycidyl ether ("jER825" (trade name) manufactured by Mitsubishi Chemical Corporation), epoxy equivalent: 170) serving as a base and 17.4 parts by mass of a polyamine compound (B-1) (1,6-hexanediamine (manufactured by Tokyo Chemical Industry Co., Ltd., active hydrogen equivalent: 29) serving as a curing agent were defoamed for 3 minutes with stirring at 2000 rpm under a reduced pressure of 1.0 Pa at room temperature to prepare a base/curing agent mixture of an adhesive for an endoscope of Example 1.

Preparation of Base/Curing Agent Mixture of Adhesive for Endoscope (Examples 2 to 23 and Comparative Examples 1 to 6)

Base/curing agent mixtures of adhesives for an endoscope of Examples 2 to 23 and Comparative Examples 1 to 6 were prepared in the same manner as the adhesive for an endoscope of Example 1 except that the composition was changed as shown in Table I given below.

Preparation of Bonded Sample (Example 1) for Hydrogen Peroxide Plasma Resistance Testing Using the mixture of Example 1, two polyurethane sheets (manufactured by Ohtsu Chemical Co., Ltd., hardness: A90, length: 70 mm, width: 5 mm, thickness: 1.0 mm) were bonded together. The adhesive for an endoscope of Example 1 was cured by heating at 80° C. for 6 hours to thereby prepare a sample (resin-resin sample) for STERRAD sterilization resistance testing. The sheets were bonded together such that an area 5 mm from one longitudinal end of one sheet and an area 5 mm from one longitudinal end of the other sheet overlap each other. The area of the bonding was 5 mm long and 5 mm wide, and the thickness of the cured adhesive was 0.125 mm.

Using the above polyurethane sheet and a stainless-steel plate (SUS 304 stainless-steel, length: 70 mm, width: 5 mm, thickness: 1.0 mm), a STERRAD sterilization resistance test sample (SUS-resin sample) was prepared in the same manner as the resin-resin sample.

Preparation of Bonded Samples (Examples 2 to 23 and Comparative Examples 1 to 6) for Hydrogen Peroxide Plasma Resistance Testing Resin-resin samples and SUS-resin samples of Examples 2 to 23 and Comparative Examples 1 to 6 were prepared in the same manner as the resin-resin sample and the SUS-resin sample of Example 1 except that mixtures of Examples and Comparative Examples were used and that the curing temperature and the curing time were changed as shown in Table I given below.

Hydrogen Peroxide Plasma Resistance Test

Using a STERRAD NX (trade name, manufactured by Johnson & Johnson) advanced course, a hydrogen peroxide plasma sterilization treatment was performed on the above two types of samples at room temperature. Using a Tensilon universal material testing instrument RTF-1210 (trade name, manufactured by A & D Company, Limited), an elongation tensile test was performed on the sample before the sterilization treatment and the sample subjected to the sterilization treatment 100 times. The sheets were pulled in the opposite longitudinal directions. The test was performed at a tensile speed of 20 mm/min and a chuck distance of 45 mm. The change in breaking strength before and after the sterilization treatment was evaluated. The test was performed with reference to JIS K6850: 1999. The evaluation was performed according to the following evaluation criteria. In this test, A, B, and, C are acceptable.

Evaluation Criteria

A: The breaking strength was 95% or more of initial breaking strength.

B: The breaking strength was 90% or more and less than 95% of initial breaking strength.

C: The breaking strength was 85% or more and less than 90% of initial breaking strength.

D: The breaking strength was less than 85% of initial breaking strength.

E: The sample was degraded and broken during a hydrogen peroxide plasma sterilization treatment, and a tensile test could not be performed.

[Lesser decreases indicate that the cured product has undergone less oxidation degradation.]

Injectability

The mixtures prepared above were each injected in an amount of 1 mL into a polyurethane tube (inner diameter: 1 mm, outer diameter: 1.8 mm, length: 100 mm, manufactured by MISUMI Corporation), and the ease of injection was evaluated according to the following evaluation criteria. The test was performed at room temperature. In this test, A and B are acceptable.

Evaluation Criteria

A: The adhesive was successfully injected into a tube within 20 seconds.

B: The adhesive stayed at a tip of a tube for 20 seconds or more but was successfully injected within 1 minute.

C: The adhesive stayed at a tip of a tube for 1 minute or more and was unsuccessfully injected.

TABLE 1

| | | Example 1 | Example 2 | Example 3 | Example 4 | Example 5 | Example 6 |
|---|---|---|---|---|---|---|---|
| Epoxy resin (A) | Type | (A-1) | (A-2) | (A-3) | (A-4) | (A-5) | (A-6) |
| | Content [parts by mass] | 100 | 100 | 100 | 100 | 100 | 100 |
| Polyamine compound (B) | Type | (B-1) | (B-1) | (B-1) | (B-1) | (B-1) | (B-1) |
| | Content [parts by mass] | 17.4 | 15.6 | 12.9 | 17.4 | 17.4 | 13.0 |
| | Equivalence ratio of active hydrogen to epoxy equivalent | 1.0 | 1.0 | 1.0 | 1.0 | 1.0 | 1.0 |
| Curing temperature | ° C. | 80 | 80 | 80 | 80 | 80 | 80 |
| Curing time | hr | 6 | 6 | 6 | 6 | 6 | 6 |
| Hydrogen peroxide plasma resistance | Resin-resin sample | C | C | C | C | C | C |
| | Resin-SUS sample | A | A | A | A | A | B |
| | Injectability | A | A | A | A | A | A |

| | | Example 7 | Example 8 | Example 9 | Example 10 | Example 11 | Example 12 |
|---|---|---|---|---|---|---|---|
| Epoxy resin (A) | Type | (A-7) | (A-2) | (A-2) | (A-2) | (A-2) | (A-2) |
| | Content [parts by mass] | 100 | 100 | 100 | 100 | 100 | 100 |
| Polyamine compound (B) | Type | (B-1) | (B-2) | (B-3) | (B-4) | (B-5) | (B-6) |
| | Content [parts by mass] | 28.0 | 26.9 | 21.3 | 15.3 | 19.1 | 53.8 |
| | Equivalence ratio of active hydrogen to epoxy equivalent | 1.0 | 1.0 | 1.0 | 1.0 | 1.0 | 1.0 |

TABLE 1-continued

| | | | | | | | |
|---|---|---|---|---|---|---|---|
| Curing temperature | ° C. | 80 | 80 | 80 | 80 | 80 | 80 |
| Curing time | hr | 6 | 6 | 6 | 6 | 6 | 6 |
| Hydrogen peroxide plasma resistance | Resin-resin sample | C | C | C | B | B | C |
| | Resin-SUS sample | B | A | A | A | A | A |
| | Injectability | A | A | A | B | B | B |

| | | Example 13 | Example 14 | Example 15 | Example 16 | Example 17 | Example 18 |
|---|---|---|---|---|---|---|---|
| Epoxy resin (A) | Type | (A-2) | (A-2) | (A-2) | (A-2) | (A-2) | (A-2) |
| | Content [parts by mass] | 100 | 100 | 100 | 100 | 100 | 100 |
| Polyamine compound (B) | Type | (B-7) | (B-8) | (B-1) | (B-1) | (B-1) | (B-1) |
| | Content [parts by mass] | 39.4 | 15.6 | 23.4 | 12.5 | 7.8 | 4.7 |
| Equivalence ratio of active hydrogen to epoxy equivalent | | 1.0 | 1.0 | 1.5 | 0.8 | 0.5 | 0.3 |
| Curing temperature | ° C. | 80 | 80 | 80 | 80 | 80 | 80 |
| Curing time | hr | 6 | 6 | 6 | 6 | 12 | 12 |
| Hydrogen peroxide plasma resistance | Resin-resin sample | C | C | C | C | C | C |
| | Resin-SUS sample | A | A | A | A | A | A |
| | Injectability | B | A | A | A | A | B |

| | | Example 19 | Example 20 | Example 21 | Example 22 | Example 23 |
|---|---|---|---|---|---|---|
| Epoxy resin (A) | Type | (A-2) | (A-2) | (A-2) | (A-2) | (A-2) |
| | Content [parts by mass] | 100 | 100 | 100 | 100 | 100 |
| Polyamine compound (B) | Type | (B-1) | (B-1) | (B-1) | (B-9) | (B-10) |
| | Content [parts by mass] | 15.6 | 15.6 | 15.6 | 14.5 | 28.5 |
| Equivalence ratio of active hydrogen to epoxy equivalent | | 1.0 | 1.0 | 1.0 | 1.0 | 1.0 |
| Curing temperature | ° C. | 120 | 40 | 25 | 80 | 80 |
| Curing time | hr | 2 | 12 | 24 | 12 | 12 |
| Hydrogen peroxide plasma resistance | Resin-resin sample | C | C | C | C | C |
| | Resin-SUS sample | A | A | A | A | A |
| | Injectability | A | A | A | B | B |

TABLE 2

| | | Comparative Example 1 | Comparative Example 2 | Comparative Example 3 | Comparative Example 4 | Comparative Example 5 | Comparative Example 6 |
|---|---|---|---|---|---|---|---|
| Epoxy resin (A) | Type | (A-2) | (A-2) | (A-3) | (A-4) | (A-5) | (A-6) |
| | Content [parts by mass] | 100 | 100 | 100 | 100 | 100 | 100 |
| Polyamine compound (B) | Type | (C-1) | (C-2) | (C-3) | (C-4) | (C-5) | (C-6) |
| | Content [parts by mass] | 18.8 | 50.0 | 27.3 | 15.6 | 31.9 | 39.8 |
| Equivalence ratio of active hydrogen to epoxy equivalent | | 1.0 | unmeasurable | 1.0 | 1.0 | 1.0 | 1.0 |
| Curing temperature | ° C. | 80 | 80 | 80 | 80 | 80 | 80 |
| Curing time | hr | 6 | 6 | 6 | 6 | 12 | 12 |
| Hydrogen peroxide plasma resistance | Resin-resin sample | D | D | D | D | D | D |
| | Resin-SUS sample | E | E | D | E | E | E |
| | Injectability | C | C | C | C | C | C |

Notes of Table
Epoxy compound (A)

(A-1) Bisphenol A diglycidyl ether ("jER825" (trade name) manufactured by Mitsubishi Chemical Corporation, epoxy equivalent: 170)

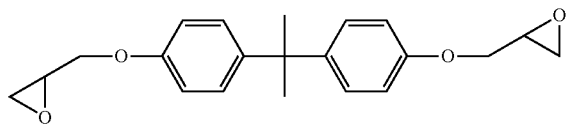 [SMILES: CC(C)(c1ccc(OCC2CO2)cc1)c1ccc(OCC2CO2)cc1]

(A-2) Bisphenol A diglycidyl ether ("jER828" (trade name) manufactured by Mitsubishi Chemical Corporation, epoxy equivalent: 190)

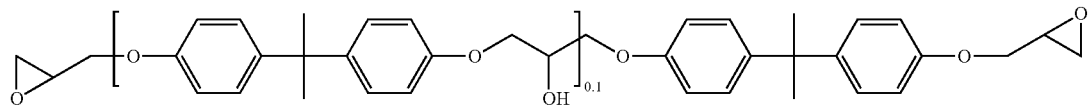

(A-3) Bisphenol A diglycidyl ether ("jER834" (trade name) manufactured by Mitsubishi Chemical Corporation, epoxy equivalent: 230)

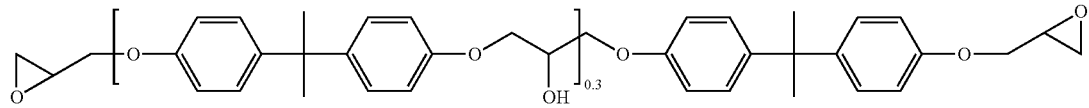

(A-4) Bisphenol F diglycidyl ether ("EPICLON 830" (trade name) manufactured by DIC Corporation, epoxy equivalent: 170)

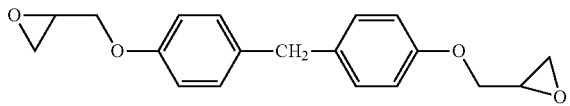 [SMILES: c1cc(OCC2CO2)ccc1Cc1ccc(OCC2CO2)cc1]

(A-5) Epoxy novolac resin (manufactured by Sigma-Aldrich, product number 406775, epoxy equivalent: 170)

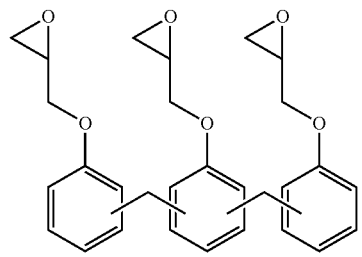

(A-6) Bisphenol A propoxylate diglycidyl ether (manufactured by Sigma-Aldrich, epoxy equivalent: 228)

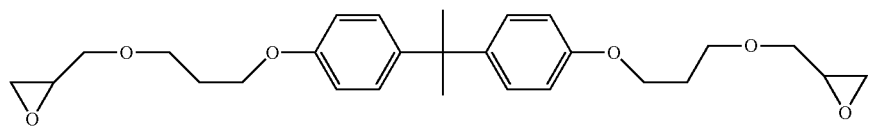

(A-7) 4,4'-Methylenebis(N,N-diglycidylaniline) (manufactured by Tokyo Chemical Industry Co., Ltd., epoxy equivalent: 106)

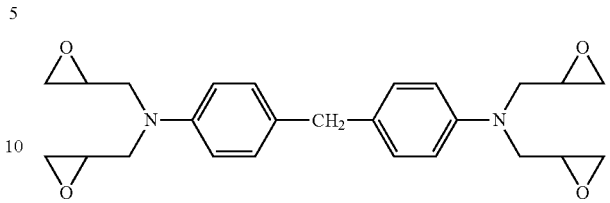

Polyamine Compound (B)

(B-1) 1,6-Hexanediamine (manufactured by Tokyo Chemical Industry Co., Ltd., active hydrogen equivalent: 29)

(B-2) 1,12-Dodecanediamine (manufactured by Tokyo Chemical Industry Co., Ltd., active hydrogen equivalent: 50)

(B-3) Trimethylhexamethylenediamine (manufactured by Tokyo Chemical Industry Co., Ltd., active hydrogen equivalent: 40)

(B-4) 1,3-Cyclohexanediamine (manufactured by Tokyo Chemical Industry Co., Ltd., active hydrogen equivalent: 29)

(B-5) 1,3-Bis(aminomethyl)cyclohexane (manufactured by Mitsubishi Gas Chemical Company, Inc., active hydrogen equivalent: 36)

(B-6) Polyoxyalkylenediamine D400 (trade name, manufactured by Mitsui Fine Chemicals, Inc., active hydrogen equivalent: 100)

(B-7) Polyoxyalkylenetriamine T403 (trade name, manufactured by Mitsui Fine Chemicals, Inc., active hydrogen equivalent: 73)

(B-8) 2-Methylpentamethylenediamine (manufactured by Tokyo Chemical Industry Co., Ltd., active hydrogen equivalent: 29)

(B-9) m-Phenylenediamine (manufactured by Tokyo Chemical Industry Co., Ltd., active hydrogen equivalent: 27)

(B-10) 4,4'-Ethylenedianiline (manufactured by Tokyo Chemical Industry Co., Ltd., active hydrogen equivalent: 53) Compounds used in Comparative Examples (C-1) m-Xylylenediamine (manufactured by Tokyo Chemical Industry Co., Ltd., active hydrogen equivalent: 34)

(C-2) Polyamidoamine curing agent, Hardner HV-953U (trade name, manufactured by Nagase ChemteX Corporation, active hydrogen equivalent: unknown)

(C-3) Isophoronediamine (manufactured by Tokyo Chemical Industry Co., Ltd., active hydrogen equivalent: 43)

(C-4) Triethylenetetramine (manufactured by Tokyo Chemical Industry Co., Ltd., active hydrogen equivalent: 24.4)

(C-5) 4,4'-Diaminodiphenylmethane (manufactured by Tokyo Chemical Industry Co., Ltd., active hydrogen equivalent: 49.6)

(C-6) 4,4'-Diaminodiphenylsulfone (manufactured by Tokyo Chemical Industry Co., Ltd., active hydrogen equivalent: 62.0)

As shown in the above Tables, when adhesives not satisfying the requirements of the present invention were used, the hydrogen peroxide plasma resistance of a resin-SUS sample was comparable (Comparative Example 3) or inferior (Comparative Examples 1, 2, and 4 to 6) to the hydrogen peroxide plasma resistance of a resin-resin sample. The injectability was unacceptable in any of Comparative Examples 1 to 6.

By contrast, when the adhesives according to the present invention were used, the hydrogen peroxide plasma resistance of a resin-resin sample was at acceptable levels, and in addition, the hydrogen peroxide plasma resistance of a resin-SUS sample was superior (Examples 1 to 23) to the hydrogen peroxide plasma resistance of a resin-resin sample (despite the generation of dissociated metal ions due to hydrogen peroxide). The injectability was at acceptable levels in Examples 1 to 23.

These results show that since oxidation degradation is effectively suppressed, the adhesive according to the present invention is suitable for bonding of constituent metal members of an endoscope and is also suitable for application to optical members that require transparency, such as bonding of resin to glass, glass to glass, and glass to metal.

While the present invention has been described in connection with embodiments thereof, we do not intend to limit our invention in any detail of the description unless otherwise specified. Rather, the invention should be broadly construed without departing from the spirit and scope of the invention as defined by the appended claims.

REFERENCE SIGNS LIST 2 electronic endoscope (endoscope)
3 insertion section
  3a flexible tube
  3b angle portion
  3c tip portion
5 main-body operation section
6 universal cord
11 spiral tube
  11a metal strip
12 tubular net
13 cap
14 flexible tube substrate
  14a distal side
  14b proximal side
15 resin layer
16 coat layer
17 cured adhesive layer
31 illumination window
32 observation window
33 forceps port
34 nozzle
35 tip-portion main body
36 end cap
37 lens holder
38 prism
39 substrate
40 solid-state imaging element
41 cured adhesive
42 cured adhesive
43 observation unit
A air layer
L1 to L5 lens

What is claimed is:

1. A method, comprising:
fixing at least one of a metal member or a glass member constituting an endoscope with a two-component adhesive,
the two-component adhesive comprising:
a base that includes at least one epoxy resin (A) selected from the group consisting of bisphenol A epoxy resins, bisphenol F epoxy resins, and phenol novolac epoxy resins; and
a curing agent that includes at least one polyamine compound (B) represented by general formula (I) or (II),

$$H_2N-L^1-(-NH_2)_n \qquad \text{general formula (I)}$$

$$H_2N-L^3-L^2-L^4-NH_2 \qquad \text{general formula (II)}$$

where in general formula (I), n represents an integer of 1 to 3, and $L^1$ represents an aliphatic or alicyclic hydrocarbon group with a valence of (n+1), an aromatic hydrocarbon group with a valence of (n+1), or a group with a valence of (n+1) having an aliphatic hydrocarbon chain into which at least one oxygen atom is incorporated, provided that when n is 1, the aliphatic or alicyclic hydrocarbon group represented by $L^1$ is a linear alkylene group having 5 to 12 carbon atoms, a cyclic alkylene group having 5 to 12 carbon atoms, or an alkylene group having 5 to 12 carbon atoms constituted by a linear alkylene group and a cyclic alkylene group, and when n is 1 and the hydrocarbon group is an alicyclic saturated hydrocarbon group, the alicyclic saturated hydrocarbon group does not include a quaternary carbon atom as an annular atom, and
in general formula (II), $L^2$ represents an alkylene group having 2 or more carbon atoms, —O—, or a divalent group having a combination thereof, and $L^3$ and $L^4$ each independently represent an arylene group, and
wherein the at least one polyamine compound (B) does not include xylylenediamine.

2. The method according to claim 1, wherein the adhesive fixes a member in a tip portion of an insertion section of the endoscope.

3. The method according to claim 2, wherein the adhesive seals peripheries of an observation window and an illumination window in the tip portion of the insertion section of the endoscope.

4. The method according to claim 2, wherein the adhesive fixes a prism in an optical device constituting the endoscope.

5. The method according to claim 1, wherein the adhesive is a mixture of the base and the curing agent with the polyamine compound (B) being present in an amount of 10 to 75 parts by mass based on 100 parts by mass of the epoxy resin (A).

6. A cured product, comprising the adhesive that was formed by curing the adhesive that fixes the at least one of a metal member or a glass member according to the method of claim 1.

7. The method according to claim 1, wherein
in a case where $L^1$ represents an aromatic hydrocarbon group with a valence of (n+1) and n is 1, the aromatic hydrocarbon group is an arylene group;
in a case where $L^1$ represents an aromatic hydrocarbon group with a valence of (n+1) and n is 2, the aromatic hydrocarbon group is an arenetriyl group; and
in a case where $L^1$ represents an aromatic hydrocarbon group with a valence of (n+1) and n is 3, the aromatic hydrocarbon group is an arenetetrayl group.

8. The method according to claim 7, wherein
the arylene group is a phenylene group or a naphthylene group,
the arenetriyl group is a benzenetriyl group or a naphthalenetriyl group, and
the arenetetrayl group is a benzenetetrayl group or a naphthalenetetrayl group.

9. An endoscope comprising:
at least one of a metal member or a glass member,
wherein the at least one of the metal member or the glass member is fixed with a two-component adhesive by curing the two-component adhesive,
the two-component adhesive comprising:
a base that includes at least one epoxy resin (A) selected from the group consisting of bisphenol A epoxy resins, bisphenol F epoxy resins, and phenol novolac epoxy resins; and
a curing agent that includes at least one polyamine compound (B) represented by general formula (I) or (II),

  general formula (I)

  general formula (II)

where in general formula (I), n represents an integer of 1 to 3, and $L^1$ represents an aliphatic or alicyclic hydrocarbon group with a valence of (n+1), an aromatic hydrocarbon group with a valence of (n+1), or a group with a valence of (n+1) having an aliphatic hydrocarbon chain into which at least one oxygen atom is incorporated, provided that when n is 1, the aliphatic or alicyclic hydrocarbon group represented by $L^1$ is a linear alkylene group having 5 to 12 carbon atoms, a cyclic alkylene group having 5 to 12 carbon atoms, or an alkylene group having 5 to 12 carbon atoms constituted by a linear alkylene group and a cyclic alkylene group, and when n is 1 and the hydrocarbon group is an alicyclic saturated hydrocarbon group, the alicyclic saturated hydrocarbon group does not include a quaternary carbon atom as an annular atom, and
in general formula (II), $L^2$ represents an alkylene group having 2 or more carbon atoms, —O—, or a divalent group having a combination thereof, and $L^3$ and $L^4$ each independently represent an arylene group, and
wherein the at least one polyamine compound (B) does not include xylylenediamine.

10. The endoscope according to claim 9, wherein the adhesive fixes a member in a tip portion of an insertion section of the endoscope.

11. The endoscope according to claim 10, wherein the adhesive seals peripheries of an observation window and an illumination window in the tip portion of the insertion section of the endoscope.

12. The endoscope according to claim 10, wherein the adhesive fixes a prism in an optical device constituting the endoscope.

13. The endoscope according to claim 9, wherein the adhesive is in the form of a mixture of the base and the curing agent with the polyamine compound (B) being present in an amount of 10 to 75 parts by mass based on 100 parts by mass of the epoxy resin (A).

14. A method for producing an endoscope, comprising:
fixing at least one of a metal member or a glass member with a two-component adhesive to form the endoscope, the two-component adhesive comprising:
a base that includes at least one epoxy resin (A) selected from the group consisting of bisphenol A epoxy resins, bisphenol F epoxy resins, and phenol novolac epoxy resins; and
a curing agent that includes at least one polyamine compound (B) represented by general formula (I) or (II),

  general formula (I)

  general formula (II)

where in general formula (I), n represents an integer of 1 to 3, and $L^1$ represents an aliphatic or alicyclic hydrocarbon group with a valence of (n+1), an aromatic hydrocarbon group with a valence of (n+1), or a group with a valence of (n+1) having an aliphatic hydrocarbon chain into which at least one oxygen atom is incorporated, provided that when n is 1, the aliphatic or alicyclic hydrocarbon group represented by $L^1$ is a linear alkylene group having 5 to 12 carbon atoms, a cyclic alkylene group having 5 to 12 carbon atoms, or an alkylene group having 5 to 12 carbon atoms constituted by a linear alkylene group and a cyclic alkylene group, and when n is 1 and the hydrocarbon group is an alicyclic saturated hydrocarbon group, the alicyclic saturated hydrocarbon group does not include a quaternary carbon atom as an annular atom, and
in general formula (II), $L^2$ represents an alkylene group having 2 or more carbon atoms, —O—, or a divalent group having a combination thereof, and $L^3$ and $L^4$ each independently represent an arylene group, and
wherein the at least one polyamine compound (B) does not include xylylenediamine.

15. The method according to claim 14, wherein the adhesive fixes a member in a tip portion of an insertion section of the endoscope.

16. The method according to claim 15, wherein the adhesive seals peripheries of an observation window and an illumination window in the tip portion of the insertion section of the endoscope.

17. The method according to claim 15, wherein the adhesive fixes a prism in an optical device constituting the endoscope.

18. The method according to claim 14, wherein the adhesive is in the form of a mixture of the base and the curing agent with the polyamine compound (B) being present in an amount of 10 to 75 parts by mass based on 100 parts by mass of the epoxy resin (A).

* * * * *